United States Patent
Summers

(10) Patent No.: US 10,869,842 B1
(45) Date of Patent: Dec. 22, 2020

(54) TRANSDERMAL DELIVERY OF PHARMACEUTICAL AGENTS

(71) Applicant: David P Summers, Montgomery, TX (US)

(72) Inventor: David P Summers, Montgomery, TX (US)

( * ) Notice: Subject to any disclaimer, the term of this patent is extended or adjusted under 35 U.S.C. 154(b) by 0 days.

(21) Appl. No.: 15/698,536

(22) Filed: Sep. 7, 2017

Related U.S. Application Data

(60) Provisional application No. 62/384,708, filed on Sep. 7, 2016, provisional application No. 62/397,804, filed on Sep. 21, 2016, provisional application No. 62/489,555, filed on Apr. 25, 2017.

(51) Int. Cl.
*A61K 9/70* (2006.01)
*A61K 31/557* (2006.01)
*A61K 31/352* (2006.01)

(52) U.S. Cl.
CPC .......... *A61K 9/7084* (2013.01); *A61K 9/7092* (2013.01); *A61K 31/352* (2013.01); *A61K 31/557* (2013.01)

(58) Field of Classification Search
CPC .. A61K 9/7084; A61K 9/7092; A61K 31/557; A61K 31/352
See application file for complete search history.

(56) References Cited

U.S. PATENT DOCUMENTS

| | | | | |
|---|---|---|---|---|
| 2002/0034535 A1* | 3/2002 | Kleiner | ........... | A61K 9/7084 424/424 |
| 2011/0150976 A1* | 6/2011 | Levin | ........... | A61K 9/0014 424/449 |
| 2012/0220980 A1* | 8/2012 | Ross | ........... | A61M 5/14248 604/506 |
| 2015/0182473 A1* | 7/2015 | Bosnyak | ........... | A61K 9/703 514/356 |

OTHER PUBLICATIONS

Biocompatible entry—Dorland's Medical Dictionary 2007 (Year: 2007).*

* cited by examiner

*Primary Examiner* — Mina Haghighatian
(74) *Attorney, Agent, or Firm* — Nick A Nichols, Jr.

(57) ABSTRACT

A method of administering a pharmaceutical agent to the circulatory system through the skin of a mammal may include the steps of loading a pharmaceutical agent in a transdermal patch, applying the transdermal patch to the skin of the mammal and releasing the pharmaceutical agent into the circulatory system at a rate of at least 0.001 micrograms per hour up to 50.0 micrograms per hour per kilogram of bodyweight of the mammal. The drug delivery system may comprise a transdermal patch loaded with the pharmaceutical agent. The patch may include a porous membrane and an outer impermeable cover defining a cavity therebetween. A plurality of drug delivery layers may be disposed between the porous membrane and the impermeable cover. A lipophilic/hydrophilic suspension may be disposed between the drug delivery layers.

12 Claims, 2 Drawing Sheets

TRANSDERMAL DELIVERY OF PHARMACEUTICAL AGENTS

CROSS-REFERENCE TO RELATED APPLICATION

This application claims the benefit of U.S. Provisional Application Ser. No. 62/384,708, filed Sep. 7, 2016, U.S. Provisional Application Ser. No. 62/397,804, filed Sep. 21, 2016, and U.S. Provisional Application Ser. No. 62/489,555, filed Apr. 25, 2017, which applications are incorporated herein by reference in their entirety.

BACKGROUND

The present invention relates to transdermal delivery of pharmaceutical agents, more particularly to a transdermal patch for administering biologically active compounds, such as but without limitation, a pharmaceutical mixture of a liposomal prostaglandin, prostaglandin derivative, prostaglandin prodrug, or mixture thereof, *cannabis* THC, cannabinols, prostaglandins and other lipophilic fatty acids, through the skin of a mammal.

Transdermal drug delivery has become a common method of administering a drug or pharmaceutical agent. Transdermal patches are typically used to administer a drug through the skin of a patient at a controlled rate. Matrix type transdermal patches not only carry the pharmaceutical agent but also attach the patch to the skin of the patient. An adhesive matrix type transdermal patch typically includes an impermeable backing, an adhesive layer and a removable protective liner. Pharmaceutical agents may be mixed in the adhesive layer and the patch applied to the skin of a patient to deliver a dose of a pharmaceutical agent through the skin and into the bloodstream of the patient.

Prostaglandins are cyclic, oxygenated fatty acids known to be potent pharmacological agents and to have a potent effect on cell function in many organ systems. Prostaglandin E1 (PGE1), for example, has various pharmacological properties, the most notable being vasodilation, inhibition of platelet aggregation, and stimulation of intestinal and uterine smooth muscle. Major disadvantages of PGE1, however, are its short in-vivo half-life of approximately 30 to 90 seconds, instability, and rapid degradation. When administered intravenously, PGE1 is rapidly metabolized during circulation through the lungs so that its pharmacological effects are significantly diminished by the time it reaches a target site or organ system.

Encapsulation of PGE1 in liposomes solves the problems of instability, short term half-line and rapid degradation experienced with PGE1 in its free form. Liposomes may function as sustained release systems for drugs, and the rate of release may be manipulated. A liposomal formulation of pharmaceutical agents results in a more effective targeted delivery, enabling delivery of the maximum patient tolerated dosage with fewer side effects.

Phytocannabinoids have efficacy in the treatment of various chronic pain conditions with greatest promise as a therapeutic adjunct in treating peripheral and central neuropathic pain and inflammation-mediated chronic pain. However, the smoked route of administration and the psychoactivity of THC, with associated concerns about abuse and long-term cognitive adverse effects, continue to pose serious and significant barriers to obtaining benefit from *cannabis* among most patients and acceptability among health care professionals and regulatory agencies.

It is therefore an object of the present disclosure to provide methods and a transdermal patch for the administration of a pharmaceutical agent, such as, but without limitation, PGE1 in liposomal or raw form, *cannabis* THC, cannabinols, prostaglandins and other lipophilic fatty acids, in liposomal or raw form, through the skin and into the bloodstream of a patient.

SUMMARY

A method of administering a pharmaceutical agent to the circulatory system through the skin of a mammal may include the steps of loading a pharmaceutical agent in a transdermal patch, applying the transdermal patch to the skin of the mammal and releasing the pharmaceutical agent into the circulatory system at a rate of at least 0.001 micrograms per hour up to 50.0 micrograms per hour per kilogram of bodyweight of the mammal.

In one embodiment, a drug delivery system may comprise a transdermal patch loaded with a pharmaceutical agent. The patch may include a porous membrane and an outer impermeable cover defining a cavity therebetween. A plurality of drug delivery layers may be disposed between the porous membrane and the impermeable cover. A lipophilic/hydrophilic suspension may be disposed between the drug delivery layers.

BRIEF DESCRIPTION OF THE DRAWINGS

So that the manner in which the above recited features, advantages and objects of the present invention are attained can be understood in detail, a more particular description of the invention briefly summarized above, may be had by reference to the embodiments thereof which are illustrated in the appended drawing.

It is noted, however, that the appended drawing illustrates only a typical embodiment of this invention and is therefore not to be considered limiting of its scope, for the invention may admit to other equally effective embodiments.

DETAILED DESCRIPTION

A transdermal drug delivery system for the administration of a pharmaceutical agent may include a transdermal patch. For purposes of illustration, but without limitation, a transdermal patch may include an impermeable backing, a drug delivery tape, an adhesive layer and a removable protective liner. Pharmaceutical agents encapsulated in a particulate drug carrier, such as liposomes, may be incorporated in the transdermal patch by methods known in the art.

Liposomes may be made of any suitable phospholipid, sphingolipid, glycolipid, derived lipid, and the like. Examples of suitable phospholipids include phosphatidylcholine, phosphatidyl serine, phosphatidie acid, phosphatidyl glycerol, phosphatidyl ethanolamine, phosphatidyl inositol, sphingomyelin, dicetyl phosphate, lysophosphatidyl choline and mixtures thereof, as well as soybean phospholipids, and egg yolk phospholipids. Suitable glycolipids include cerebroside, sulphur-containing lipids, ganglioside and the like.

Liposomes and liposheres may be formed by any of the known methods for forming liposomes and may be loaded with prostaglandin according to known procedures. Those skilled in the art will recognize that, in addition to prostaglandin, the liposomes and liposheres may be loaded with many other drugs or agents.

A transdermal patch may be loaded with pharmaceutical agents including, but not limited to, *cannabis* THC, cannabinols, prostaglandins and other lipophilic fatty acids, in liposomal or raw form, a liposomal mixture, micro particulate mixture and/or a mixture of both may carry prostaglandin, prostaglandin derivative, prostaglandin prodrug or a mixture thereof, *cannabis* THC, cannabinols, and other lipophilic fatty acids, in liposomal or raw form. The pharmaceutical agents may be compounded and designed to be delivered through the skin of a mammal, such as but without limitation, a human patient, and released into the bloodstream for the treatment of, but without limitation, cardiovascular diseases, restenosis after angioplasty, occlusive peripheral and coronary artery disease, liver disease, myocardial infarction, stroke and the like.

Figure 1:
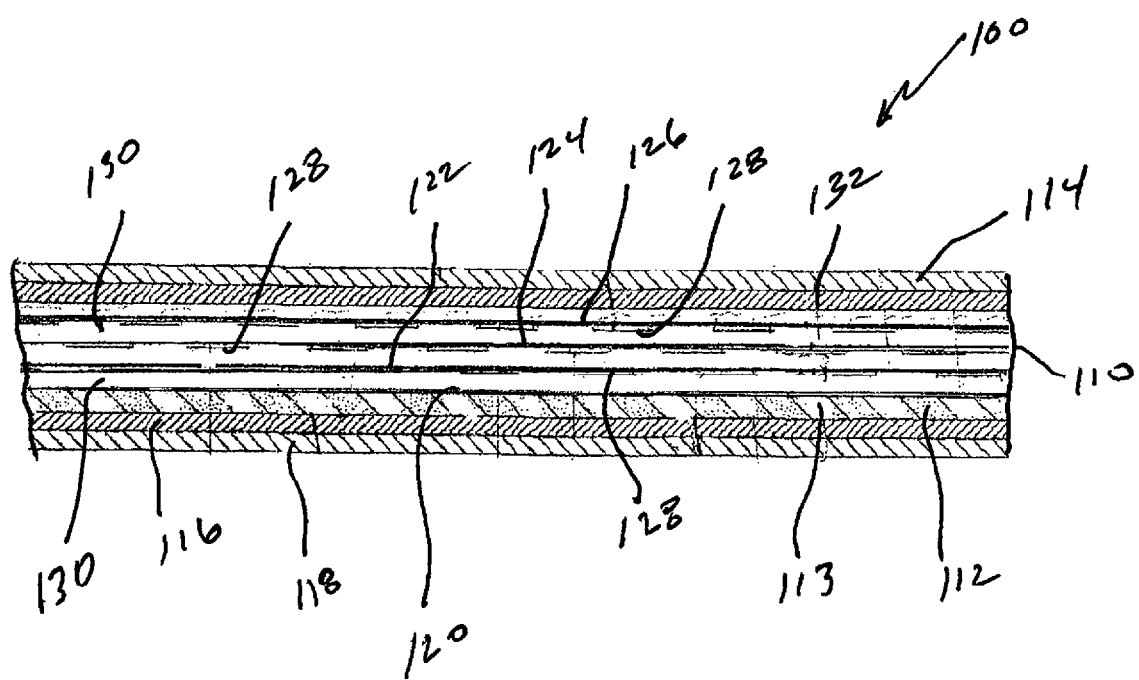
FIG. 1 is a fragmentary section view of a first embodiment of a transdermal drug delivery patch.

Referring now to FIG. 1, a transdermal drug delivery system may include a trasdermal patch generally identified by the reference numeral 100. The patch 100 may include a cavity 110 defined between a porous membrane 112 and an outer impermeable skin or cover 114. The porous membrane 112 may include a plurality of apertures 113. A layer 116 of a semi-porous adhesive may applied to a bottom surface of the membrane 112 for securing the patch 100 to the skin of a patient. A peel away liner 118 may cover the adhesive layer 116. The liner 118 may be removed prior to application of the patch 100, thereby exposing the adhesive layer 116 for securing the patch 100 to the skin of the patient.

One or more drug delivery layers for dispensing a pharmaceutical agent may be disposed in the cavity 110. The drug deliver layers may comprise one or drug delivery tapes disposed in the patch cavity 110 vertically spaced from one another. The patch 100 illustrated in FIG. 1, may include an innermost drug delivery tape 120, a secondary drug delivery tape 122, a tertiary drug delivery tape 124 and a quaternary drug delivery tape 126. Each drug delivery tape 120, 122, 124, 126 may include a plurality of micro-dots 128 of pharmaceutical agents including, but not limited to, *cannabis* THC, cannabinols, and other lipophilic fatty acids, a liposomal mixture, micro particulate mixture and/or a mixture of both carrying prostaglandin, prostaglandin derivative, prostaglandin prodrug or a mixture thereof, in liposomal or raw form, printed on the drug releasing tapes 120, 122, 124, 126.

A layer 130 of a lipophilic/hydrophilic suspension gel may be disposed between each of the drug releasing tapes 120, 122, 124, 126. A biocompatible membrane 132 may overlay the drug releasing tapes 120, 122, 124, 126. The outer impermeable skin or cover 114 may be applied over the membrane 132.

In a preferred embodiment, the transdermal patch 100 may release at least 0.001 micrograms per hour up to 50.0 micrograms per hour of a pharmaceutical agent and/or mixture thereof per one kilogram of bodyweight of the patient. More preferably, the transdermal patch 100 may release 20 micrograms per hour of the pharmaceutical agent and/or mixture thereof per kilogram bodyweight. Prostaglandins or derivatives thereof may achieve a percent (%) weight to body weight ratio of drug to blood chemistry of at least 0.001% micrograms per one kilogram of bodyweight of the patient and maintain a constant level of optimal blood circulation concentrations of up to 12 hours to 48 hours.

Figure 2:
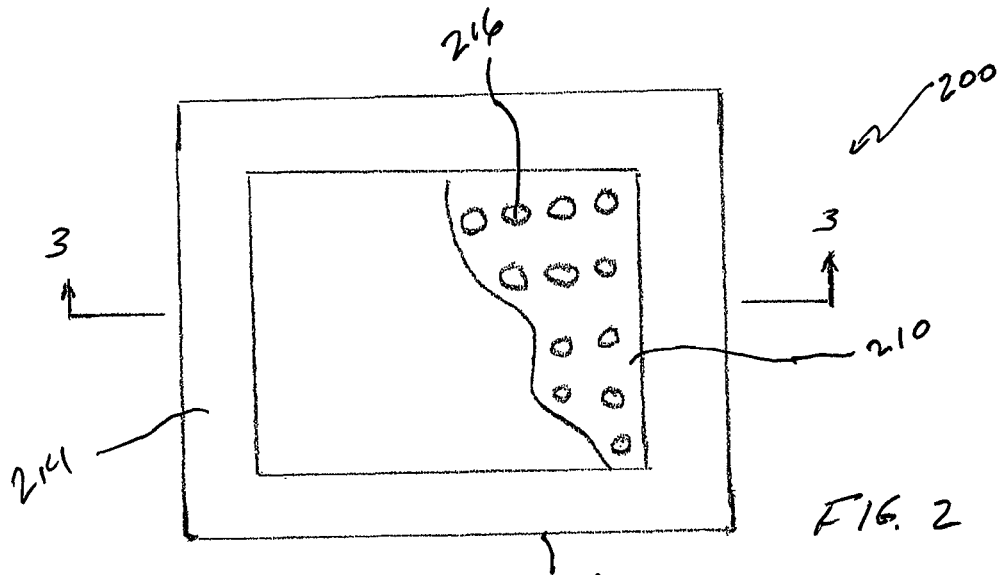
FIG. 2 is a partially broken away top plan view of a second embodiment of a transdermal drug delivery patch.
Figure 3:
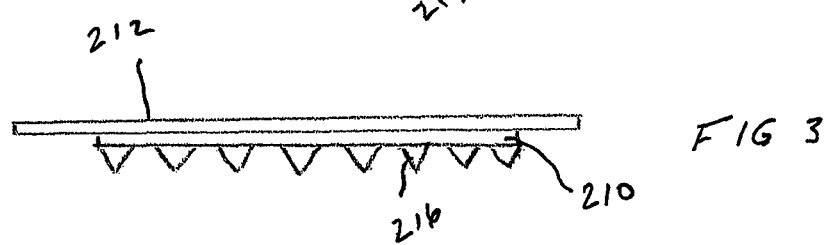
FIG. 3 is a section view taken along line 3-3 of FIG. 2.

Referring now to FIGS. 2 and 3, a second embodiment of a transdermal patch is generally identified by the reference numeral 200. The transdermal patch 200 may include a biocompatible membrane 210 covered by an impermeable cover 212. The outer dimensions of the cover 212 may extend beyond the perimeter of the membrane 210 and define a surface 214 surrounding the membrane 210. A layer of adhesive may be applied to the surface 214.

An array of polymer or micro needles 216 may be fixed to the membrane 210 in a manner known in the art. The micro needles 216 may be hollow and loaded with an appropriate dosage of pharmaceutical agents, including but not limited to, a prodrug or derivative of prostaglandin. Each micro needle 216 may contain the precise dosage required for attaining and maintaining the pharmacological levels required by the patient. A peel away liner 218 (not shown in the drawings) may extend over the tips of the micro needles 216. The liner 218 may be removed prior to application of the patch 200, thereby exposing the micro needles 216 for injection of the pharmaceutical agent into the circulatory system of the patient.

Figure 4:
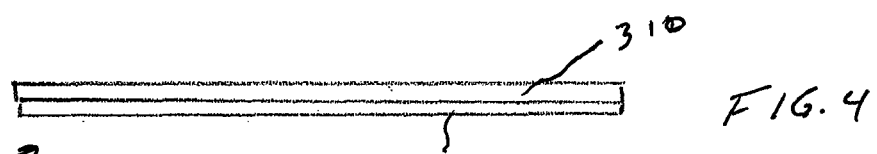
FIG. 4 is a section view of third embodiment of a transdermal drug delivery patch.

Referring now to FIG. 4, a third embodiment of a transdermal patch is generally identified by the reference numeral 300. The patch 300 may include an impermeable cover 310. Raw or generic prostaglandin (PGE1) may be loaded in an adhesive layer 312 applied to one side of the cover 310. The PGE1 may be mixed with the adhesive and/or a binder. The PGE1 may be released over a period of time by body heat melting thin layers of the PGE1 embedded in the adhesive layer 312.

Figure 5:
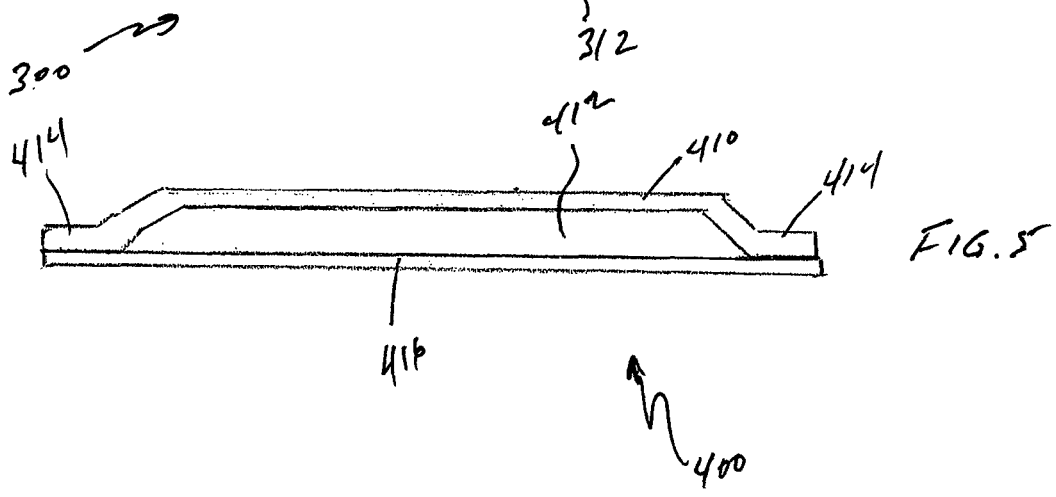
FIG. 5 is a section view of a fourth embodiment of a transdermal drug delivery patch.

A fourth embodiment of a transdermal patch, shown in FIG. 5, is generally identified by the reference numeral 400. The patch 400 may include am impermeable cover 410 configured to define a void or reservoir 412. The cover 410 may include a radially outwardly extending portion 414 circumscribing the reservoir 412. Adhesive may be applied to the bottom surface of the cover portion 414 for adhesively securing a porous membrane 416 covering the reservoir 412 to the cover 410. A peel away liner 418 releaseably attached to the membrane 416 may be removed prior to securing the patch 400 to the skin of a patient. The patch 400 may provide controlled release of raw PGE1 contained in the reservoir 412 through the porous membrane 412 covering the reservoir 412.

While preferred embodiments of a transdermal patch have been shown and described, other and further embodiments may be devised without departing from the basic scope thereof, and the scope thereof is determined by the claims which follow.

The invention claimed is:
1. A drug delivery system comprising:
   a) a transdermal patch for administering a pharmaceutical agent through the skin of a patient;
   b) said patch including a porous membrane and an outer impermeable cover defining a cavity therebetween;
   c) a layer of semi-porous adhesive applied to a bottom surface of said porous membrane;
   d) a plurality of drug delivery tapes disposed in said cavity in vertical spaced layers relative to one another;
   e) a plurality of micro-dots containing said pharmaceutical agent imprinted on each said plurality of drug delivery tapes; and f) a layer of lipophilic or hydrophilic suspension disposed between said layers of said plurality of drug delivery tapes.

2. The drug delivery system of claim 1 wherein said pharmaceutical agent is released at a rate of at least 0.001 micrograms per hour up to 50.0 micrograms per hour per kilogram of bodyweight of the patient.

3. The drug delivery system of claim 1 wherein said pharmaceutical agent is released at a rate of 20 micrograms per hour per kilogram bodyweight of the patient.

4. The drug delivery system of claim 1 wherein said porous membrane includes a plurality of apertures.

5. The drug delivery system of claim 1 wherein said pharmaceutical agent comprises *cannabis* THC.

6. The drug delivery system of claim 1 wherein said pharmaceutical agent comprises cannabinols.

7. The drug delivery system of claim 1 wherein said pharmaceutical agent comprises a liposomal prostaglandin, prostaglandin derivative, prostaglandin prodrug, or mixture thereof.

8. The drug delivery system of claim 1 wherein said pharmaceutical agent comprises a lipophilic fatty acid.

9. The drug delivery system of claim 1 further including a biocompatible membrane overlaying said plurality of drug delivery tapes.

10. The drug delivery system of claim 1 further including a removable liner overlaying said semi-porous adhesive layer.

11. The drug delivery system of claim 9 wherein said pharmaceutical agent comprises a liposomal prostaglandin, prostaglandin derivative, prostaglandin prodrug, or mixture thereof.

12. The delivery system of claim 9 wherein said pharmaceutical agent comprises *cannabis* THC, cannabinols, or prostaglandins in liposomal or raw form.

* * * * *